United States Patent [19]
Franks et al.

[11] Patent Number: 6,071,428
[45] Date of Patent: Jun. 6, 2000

[54] STABLE COMPOSITIONS

[75] Inventors: Felix Franks; Barry Aldous; Anthony Auffret, all of Cambridge, United Kingdom

[73] Assignee: Inhale Therapeutic Systems, San Carlos, Calif.

[21] Appl. No.: 08/638,479

[22] Filed: Apr. 26, 1996

[30] Foreign Application Priority Data

Apr. 28, 1995 [GB] United Kingdom ................... 9508691

[51] Int. Cl.[7] ............................. C09K 31/02; F41A 9/00; F41A 23/00; F41B 11/00
[52] U.S. Cl. ........................... 252/1; 252/182.29; 124/42; 124/29; 124/58; 124/60
[58] Field of Search .................................. 124/42, 29, 58, 124/60; 252/1, 182.29

[56] References Cited

U.S. PATENT DOCUMENTS

| | | | |
|---|---|---|---|
| 1,855,591 | 4/1932 | Wallerstein . | |
| 3,300,474 | 1/1967 | Flodin et al. | 260/209 |
| 4,206,200 | 6/1980 | Guthorstein et al. | 424/92 |
| 4,267,703 | 5/1981 | Minifie et al. | 62/123 |
| 4,457,916 | 7/1984 | Hayashi | 424/101 |
| 4,595,418 | 6/1986 | Yoshino | 127/30 |
| 4,699,882 | 10/1987 | Visuri | 435/188 |
| 4,753,816 | 6/1988 | Vink et al. | 426/660 |
| 4,892,745 | 1/1990 | Gage et al. | 426/549 |
| 4,910,135 | 3/1990 | Tischer et al. | 435/28 |
| 5,023,092 | 6/1991 | DuRoss | 426/3 |
| 5,112,407 | 5/1992 | Sakai et al. | 127/58 |
| 5,326,405 | 7/1994 | Pluim et al. | 127/42 |
| 5,549,757 | 8/1996 | Morano | 127/42 |

FOREIGN PATENT DOCUMENTS

| | | |
|---|---|---|
| 0 111 216 | 6/1984 | European Pat. Off. . |
| 0 383 569 | 8/1990 | European Pat. Off. . |
| 0 520 748 | 12/1992 | European Pat. Off. . |
| 31 41 498 | 4/1983 | Germany . |
| 60-244288 | 12/1985 | Japan . |
| WO 87/00196 | 1/1987 | WIPO . |
| WO 87/05300 | 9/1987 | WIPO . |
| WO 90/05182 | 5/1990 | WIPO . |
| WO 86/04095 | 7/1996 | WIPO . |

OTHER PUBLICATIONS

Concise Encyclopedia of Chemistry, M. Eagleson (ed.), Walter de Gruyter, Berlin, pp. 456–457, 1994.
Carpenter et al., "Stabilization of Phosphofructokinase during Air Drying with Sugars, . . . " Cryobiology 24, 455–464 (1987).
Carpenter et al., "Modes of Stabilization of a Protein by Organic Solutes during Desiccation," Cryobiolgy 25, 459–470 (1988).
White et al., "The glassy state in certain sugar–containing food products," J.Food Technol., 1, 73–82 (1966).
Schneider et al., "Thermostability of Enzyme in the Three–Dimensional Network of Polysaccharide Chains," Bulletin de l'Acad.Polonnaise des Sciences, vol.XVI, No. 4, 203–204 (1968).
van de Beek et al., "Preservation of the Enzymatic Activity of Rennin During Spray Drying and . . . ," Neth.Milk Dairy J.23, 46–51 (1969).
Townsend et al., "Use of Lyoprotectants in the Freeze–Drying of a Model Protein, Ribonuclease A," J.of Parenteral Science & Technology, 42, 190–198 (1988).

Primary Examiner—C. H. Kelly
Attorney, Agent, or Firm—Susan T. Evans; Felissa H. Cagan; Stephen L. Hurst

[57] ABSTRACT

In a composition which has an amorphous, undercooled, glassy phase containing a water-soluble or water-swellable substance in an amorphous form, a sugar, which is capable of existing as a crystalline hydrate, is used as an agent to dehydrate the amorphous phase by crystallization therefrom, and thereby enhance the glass transition temperature of the residual amorphous phase.

17 Claims, 1 Drawing Sheet

STABLE COMPOSITIONS

This application claims the benefit of priority under 35 U.S.C. § 119 to Great Britian Patent Application No. 9508691.4, filed Apr. 28, 1995.

FIELD OF THE INVENTION

This invention is concerned with compositions containing an amorphous phase which comprises a water-soluble or water-swellable material, in an undercooled amorphous form.

BACKGROUND OF THE INVENTION

A glass is defined as an undercooled liquid with a very high viscosity, that is to say at least $10^{12}$ Pa.s.

Normally a glass presents the appearance of a homogeneous, transparent, brittle solid which can be ground or milled to a powder. In a glass, diffusive processes take place at extremely low rates, such as microns per year. Diffusion-limited chemical or biochemical changes including more than one reacting moiety are severely inhibited.

Above a temperature known as the glass transition temperature $T_g$, the viscosity drops rapidly and the glass turns into a rubber (which is also an undercooled liquid), then into a deformable plastic which at even higher temperatures turns into a mobile fluid. This invention is concerned with glass forming substances which are hydrophilic and water-soluble or water-swellable so that the water will act as a plasticiser. Many hydrophilic materials, both of a monomeric and a polymeric nature either exist as, or can be converted into, amorphous states which exhibit the glass/rubber transitions characteristic of amorphous macromolecules. They have well defined glass transition temperatures $T_g$ which depend on the molecular weight and a molecular complexity of the glass forming substance. $T_g$ is depressed by the addition of diluents. Water is the universal plasticiser for all such hydrophilic materials. Therefore, the glass/rubber transition temperature is adjustable by the addition of water or an aqueous solution.

It is well known to incorporate some form of sugar into a pharmaceutical composition as an excipient. It is also well known to incorporate sugars into compositions containing unstable biological materials which are converted from dilute aqueous solution into dry products by removal of upwards of 99% of water by freeze-drying or evaporative drying from a liquid state.

European Patent 383569 (Inventores: Franks and Hatley) teaches that a variety of carbohydrates are able to stabilise bioproducts against deterioration during drying and thereafter, provided that the preparations are dried to a low residual moisture content, typically 2% by weight, so as to render them into amorphous glasses, with glass transition temperatures lying well above the maximum temperature to which the dried product will be exposed during distribution and storage. It is demonstrated that the glass state ensures long-term stability of so-called labile products, such as isolated enzymes.

When a crystallizable water-soluble material such as a carbohydrate forms an amorphous glass (below the glass transition temperature) or rubber (somewhat above the glass transition temperature) which in either case includes some moisture, the composition is both an undercooled liquid and a supersaturated solution. That is to say it is cooled below the temperature at which crystallization could begin and contains a higher concentration of crystallizable material than a saturated solution. In terms of thermodynamics, such as amorphous composition is a non-equilibrium state with respect to the equilibrium solid, i.e. the crystalline solid state.

An amorphous glassy material, e.g. a glassy carbohydrate therefore relies for its apparent long-term existence on the low probability of crystallization and low rate of crystallization. The actual glass temperature of a mixture depends, among other factors, on the details of its chemical composition and any residual moisture content, with water acting as a plasticiser, depressing the glass temperature. If at any time the glass temperature is exceeded, either by exposure to heat or in consequence of the inadvertent migration of moisture into the product, a carbohydrate excipient may become liable to irreversible phase separation by crystallization. If crystallization occurs, any residual amorphous phase will then be composed of the other components and the moisture, resulting in a major depression of the glass temperature.

Thus, a freeze-dried wholly amorphous preparation, containing 2% of a calcitonin gene-related protein, 95% lactose excipient and 3% residual moisture was found to have a glass temperature of 40° C. When the preparation was heated above this temperature, the lactose crystallised irruptively, leaving a solution phase composed of 40% protein and 60% water. The resulting preparation now exhibited a glass temperature (of the solution phase) lying below −40° C. and had lost its chemical stability at ambient temperature, and its biological activity.

SUMMARY OF THE INVENTION

This invention employs the crystallization of certain sugars from an amorphous solid preparation to raise the glass temperature of the preparation and, hence, to enhance the useful storage stability of the preparation.

The present invention requires a sugar that is able to crystallise in a hydrated form, with water molecules included in the crystalline lattice as so-called water of crystallization. In general such crystalline forms will contain a stoichiometric amount of water, so that the ratio of water molecules to sugar molecules in such crystals will have constant values.

We have appreciated that such crystallization can be utilised to abstract water from an amorphous phase, which is the remainder of the composition and moreover do so to an extent which will raise the glass transition temperature of that phase.

Accordingly, this invention provides the use of a sugar, which is capable of existing as a crystalline hydrate, in a composition having an amorphous undercooled phase containing a water-soluble or water-swellable substance in an amorphous form and also containing moisture, as an agent to dehydrate the amorphous phase by crystallization therefrom, and thereby enhance the glass transition temperature of the residual amorphous phase.

This sugar, capable of crystallizing as a hydrate will be referred to as a "hydratable sugar". It may serve to raise the glass transition temperature by 5° C. or more, possibly 10° C. or more.

When crystallization occurs, any moisture which is not taken up into the crystals becomes part of the residual amorphous phase. Consequently the amount of hydratable sugar in the composition should be large enough to abstract a high proportion of the water, and thereby achieve a residual amorphous phase with a raised glass temperature compared to that of the composition before crystallization.

The amount of hydratable sugar may be adequate to take all the water into crystals of the hydrate. Alternatively a small amount of water may remain in the residual amorphous phase, but it will generally be required that the amount of this sugar in relation to the total water content of the composition is such that the water content (if any) of the amorphous phase expressed as a percentage by weight, of that phase is a smaller percentage than the total water content of the whole composition expressed as a percentage by weight of that whole composition.

Expressed algebraically, such a composition has a total mass m and a total water content w. After crystallization of the sugar, the residual amorphous phase has a mass m' and this phase has a water content w' which, as a percentage of the amorphous phase is $$\frac{w'}{m'} \times 100\%$$

This percentage is less than $$\frac{w}{m} \times 100\%$$

which is the total water content as a percentage of the total composition.

A suitable minimum quantity of hydratable sugar to incorporate in a formulation can be found by calculation from an estimate of the water content before crystallization and the ratio of sugar to water in the crystalline hydrate. If the water content of the composition before crystallization is too high it may be necessary to reduce this by more effective drying of the composition.

Preferably the amount of hydratable sugar exceeds the amount which would theoretically be required to take up all the moisture from the composition. For this to be the case, the amount of hydratable sugar relative to moisture should exceed the stoichiometric ratio of sugar molecules to water molecules in the crystals.

Although the required minimum amount of hydratable sugar depends on the nature of this sugar and the moisture content before drying, it will often be the case that the amount of hydratable sugar (calculated as its anhydrous form) is at least 30%, possibly at least 50% by weight of the total composition.

A composition in which the glass transition temperature of an amorphous phase has been raised by crystallization of hydratable sugar represents a further aspect of this invention. This aspect of the invention can be defined as a composition containing an amorphous undercooled phase which comprises a water-soluble or water-swellable substance in an amorphous form, said amorphous phase having a glass transition temperature of at least 20° C., much better at least 30° C., said amorphous phase being present together with a crystalline sugar hydrate, the amount of this sugar in relation to the total water content of the composition being such that the water content (if any) of the amorphous phase expressed as a percentage by weight of that phase is a smaller percentage than the total water content of the whole composition expressed as a percentage of the whole composition.

Crystallization of a hydratable sugar in accordance with this invention could be utilised in a composition which would otherwise (i.e. before crystallization) have a glass transition temperature which is lower than desired, e.g. below 20° C. The crystallization would preferably be utilised to raise the glass transition temperature to above 25° C., more preferably above 30° C. or even above 40° C. Glass transition temperatures of 60° C. and above can be achieved with this invention.

This application of the invention may be employed when drying is carried out by a spray drying procedure, in which a solution to be dried is sprayed into a hot gas stream, as disclosed in European Published Application 520748. It may also be employed with other methods of drying, such as vacuum drying.

Accordingly, in one aspect, this invention provides a method of preparing a composition containing an amorphous glassy undercooled phase which comprises a water-soluble or water-swellable substance in an amorphous form, said amorphous phase having a glass transition temperature of at least 20° C., better at least 30° C. or 40° C., comprising the steps of providing an aqueous solution containing a sugar which is capable of existing as a crystalline hydrate, drying said solution to form a supersaturated amorphous composition with a residual moisture content, and allowing said sugar to crystallize, as the crystalline hydrate, from the supersaturated composition, so as to leave a residual amorphous phase, the amount of said sugar in the composition being sufficient, in relation to the total water content of the composition after drying, that crystallisation of said sugar hydrate removes water from said amorphous phase and reduces the percentage content of water therein.

Of course, the invention could be utilised to raise the glass transition temperature in this way even when initial drying achieves a glass transition temperature above 20° C. Abstraction of water from the amorphous phase by crystallisation of the sugar as a hydrate would then cause a further rise in the glass transition temperature.

Achieving a glass transition temperature is desirable because a composition in a glassy amorphous state can then tolerate exposure to higher ambient temperatures, e.g. hot climates, during distribution and storage.

It is possible that the extent of crystallisation in a composition would increase when exposed to an increase in ambient temperature, because the higher temperature would increase the rate of crystallisation.

The invention can also be employed to provide protection against migration of moisture into a composition, when it is foreseen that the dried composition with an amorphous glassy phase will or may be exposed to moisture.

The composition would be formulated and dried so as to contain some crystallizable sugar in the amorphous state. In the event that moisture did enter the composition, lowering (or tending to lower) the glass transition temperature to below the storage temperature, this moisture would be taken up by (further) crystallization of hydratable sugar, thereby maintaining (or limiting any deterioration of) the glass transition temperature. This could similarly be useful in a composition required to undergo exposure to water or steam during subsequent processing, e.g. incorporation into another product with the aid of pelleting or tableting.

So, in another aspect, this invention provides a method of preparing a composition containing an amorphous glassy undercooled phase which comprises a water-soluble or water-swellable substance in an amorphous form, said amorphous phase having a glass transition temperature of at least 20° C. better at least 30° C., comprising the steps of providing an aqueous solution containing a sugar which is capable of existing as a crystalline hydrate, drying said solution to form a supersaturated amorphous composition with a residual moisture content, and possibly allowing part of said sugar to crystallise, as the crystalline hydrate, from the supersaturated composition, then handling or storing said composition with exposure to moisture, wherein crystallisation of said sugar hydrate from the amorphous composition removes therefrom at least some moisture absorbed during said handling or storing.

In a development of this invention, it has been found that crystallisation of the sugar hydrate (or partial crystallisation limited by the amount of moisture present) can be induced by contacting the dried composition with means to initiate crystal growth, especially a seed crystal of the sugar hydrate.

A seed crystal which is added to the dried composition, so as to contact its surface, appears to induce crystal growth more effectively than tiny crystals already embedded within the amorphous glass.

BRIEF DESCRIPTION OF THE DRAWING

The sole drawing is a diagrammatic illustration of laboratory scale spray-drying apparatus.

DETAILED DESCRIPTION AND EMBODIMENTS

Figure 1:
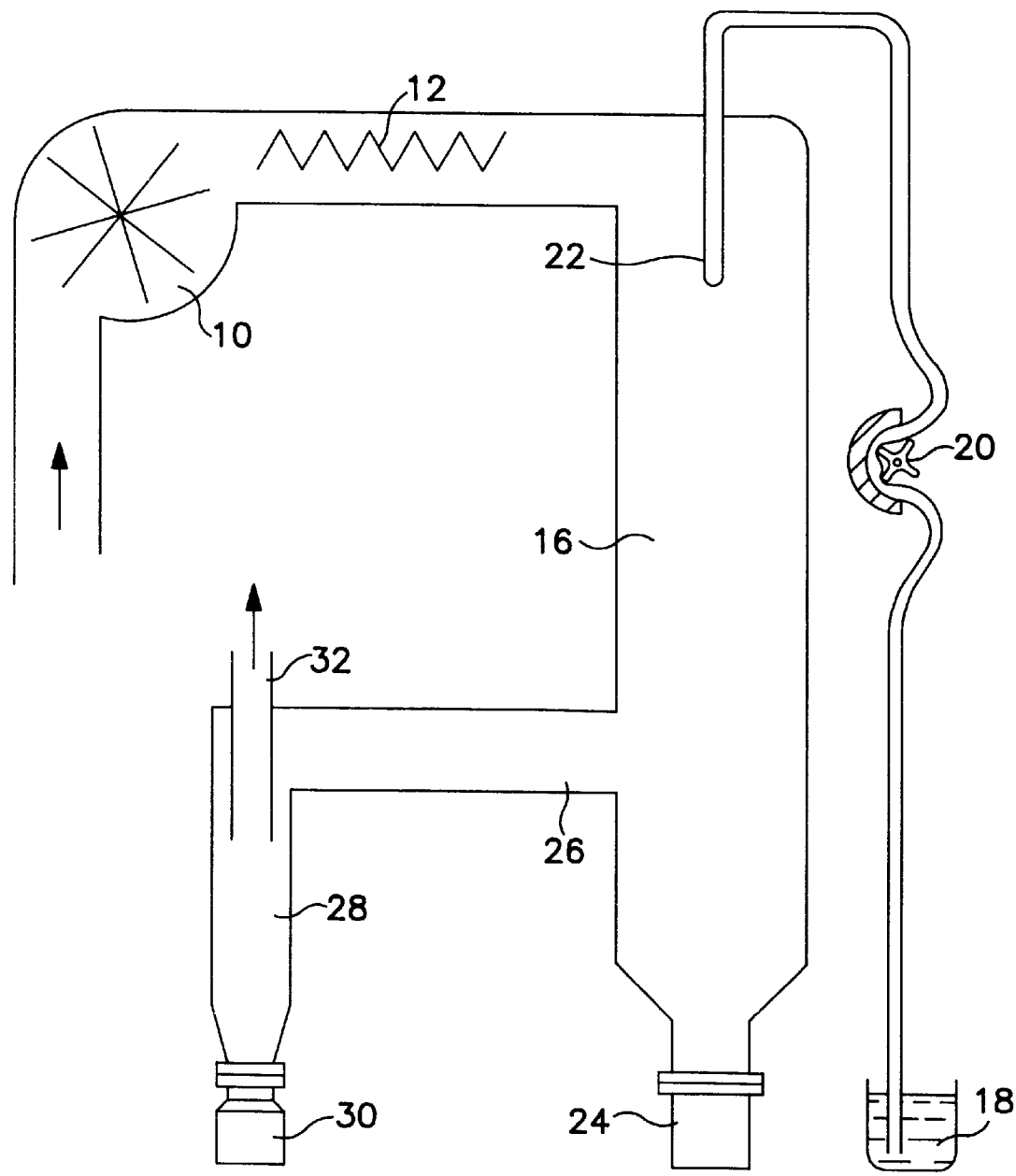

Essential to this invention is a sugar, capable of crystallizing as a hydrate. The crystalline sugar hydrate should in general be stable, i.e. should retain its water of crystallisation at 20° C. and preferably should be stable at temperatures up to at least 30° C. or 40° C. Di- and poly-hydrates are preferred over monohydrates, which take up a smaller proportion of water. However, monohydrates can be useful, notably when the residual water content after drying is low.

Sugars which form crystalline hydrates include, but are not limited to:

$\alpha,\alpha$-trehalose.$2H_2O$,
$\beta,\beta$-trehalose.$4H_2O$,
melibiose.$2H_2O$,
melezitose.$2H_2O$,
raffinose.$5H_2O$,
mannotriose.$3H_2O$ and
stachyose.$4H_2O$ In a composition according to this invention, there must be a water-soluble or water-swellable material which forms a substantial part of the (residual) amorphous phase after crystallization has taken place. It may be provided in whole or in part by the same sugar that forms a crystalline hydrate, but in an amorphous state.

The amorphous phase of the composition may, however, contain a glass forming material which does not exist in any hydrated crystalline state—at least does not do so at temperatures from 10° C. to 50° C. Such material may be a carbohydrate, e.g. maltotriose. It may be a polyhydroxy compound which is a carbohydrate derivative such as sorbitol or a chemically modified carbohydrate.

When the crystalline sugar hydrate is in a di- or polyhydrate, the amorphous phase of the composition may possibly contain a glass forming material, e.g. a sugar, which exists as a monohydrate.

Another important class of glass forming substances are water-soluble or water-swellable synthetic or natural polymers, such as polyvinyl pyrrolidone, polyacrylamide polyethyleneimine and albumin. Here $T_g$ is a function of the molecular weight. Both of these classes of glass forming substances are suitable for the present invention.

A group of glass forming substances which may in particular be employed are sugar copolymers described in U.S. Pat. No. 3,300,474 and sold by Pharmacia under the Registered Trade Mark "Ficoll". This U.S. patent describes the materials as having molecular weight 5,000 to 1,000,000 and containing sucrose residues linked through ether bridges to bifunctional groups which are not themselves carbohydrates. Such groups may be alkylene of 2, 3 or more carbon atoms but not normally more than 10 carbon atoms. The bifunctional groups serve to connect sugar residues together. These polymers may for example be made by reaction of the sugar with a halohydrin or a bis-epoxy compound.

A possibility, therefore, is that a composition will contain a substantial proportion of a glass forming material which cannot exist in a hydrated crystalline state, for instance at least 25% of the composition by weight, together with hydratable sugar. It is possible, but not necessarily the case, that some of this hydratable sugar remains in amorphous form after crystallization.

If a composition contains water-soluble material in the amorphous phase which remains after crystallization, it can be expected that the crystals of the sugar hydrate will be embedded in the glassy amorphous phase, and will be very small.

If a composition has an amorphous phase consisting of a water-swellable but water-insoluble material, it can be expected that the crystals of the sugar hydrate will form at the surface of this material and may be detachable from it.

Compositions with the features of this invention can be utilised to put into a stable form materials which are normally unstable at ambient temperature. The amorphous phase may therefore contain one or more materials which are unstable, so as to improve the storage stability of the materials.

Such material(s) stabilised for storage may potentially be any of wide range of materials which are ordinarily liable to undergo a chemical reaction which is dependent on diffusion of reacting species.

One category of materials to which the invention is applicable is proteins and peptides, including derivatives thereof such as glycoproteins. Such proteins and peptides may be any of: enzymes, transport proteins, e.g. haemoglobin, immunoglobulins, hormones, blood clotting factors and pharmacologically active proteins or peptides.

Another category of materials to which the invention is applicable comprises nucleosides, nucleotides, dinucleotides, oligonucleotides (say containing up to four nucleotides) and also enzyme cofactors, whether or not these are nucleotides. Enzyme substrates in general are materials to which the invention may be applied.

The invention may also be applied to the storage of synthetic organic compounds which exist in an amorphous form. A number of synthetic compounds, useful as pharmaceuticals, e.g. some antibiotics and which are not proteins, peptides, nucleosides or nucleotides, have only been produced in amorphous forms which may benefit from stabilization during storage.

The material for stabilisation and storage may be isolated from a natural source, animal, plant, fungal or bacterial, or may be produced by and isolated from cells grown by fermentation in artificial culture. Such cells may or may not be genetically transformed cells.

The material will need to be soluble in aqueous solution, at least to the extent of forming a dilute solution which can be used for incorporation into the glass forming substance, or alternatively the material may be dispersible in aqueous solution.

This invention may be employed to store more than one component of a reacting system in a glass. This can be useful for materials which will be required to be used together in, for example, an assay or a diagnostic kit.

Storing the materials as a single glassy preparation provides them in a convenient form for eventual use. For instance, if an assay requires a combination of a substrate, or cofactor and an enzyme, two or all three could be stored in a glass in the required concentration ratio and be ready for use in the assay.

If multiple materials are stored, they may be mixed together in an aqueous solution and then incorporated together into a glass. Alternatively they may be incorporated individually into separate glasses which are then mixed together.

When multiple materials are stored as a single composition—which may be two glasses physically mixed together as an (apparent) mixture of solids—one or more of the materials may be a protein, peptide, nucleoside, nucleotide or enzyme cofactor. It is also possible that the materials may be simpler species. For instance a standard assay procedure may require pyruvate and NADH to be present together. Both can be stored alone with acceptable stability. However, when brought together in aqueous solution they begin to react. If put together in required proportions in the glassy state they do not react and the glass can be stored.

Another possibility is that the material which is stored may comprise viable biological cells. The composition obtained can then contain the cells in a state of suspended animation, and viable cells can be recovered from storage. Cells which may be placed in a storable condition will preferably be existing as single cells, being either a single cell organism or being cells which are in culture as individual, undifferentiated cells. In particular the cells may be a bacterial culture, which may be isolated from nature or maybe a laboratory or industrial bacterial strain including genetically transformed bacteria. The cells may be eukaryotic cells, notably including yeasts but also other fungal cultures. Again the cell culture may be a natural isolate or a laboratory or industrial culture produced by fermentation including genetically transformed strains.

WO 87/000/96 proposes that materials can be stabilised using trehalose, although the formation of a crystalline hydrate of trehalose is not indicated. It is a feature of this invention that it can be implemented without reliance on $\alpha,\alpha$-trehalose (or either form of trehalose) as the only material which is present in the composition and capable of forming a glass. For instance a composition might contain some trehalose jointly with another glass-forming material which could be a second sugar. On crystallization of the trehalose as hydrate, the residual amorphous phase would contain the other glass-forming material, possibly mixed with some trehalose, in the glass state.

A hydratable sugar will generally be put to use, in accordance with this invention, by drying an aqueous solution of the sugar to an undercooled, supersaturated amorphous state, and then allowing crystallization to occur.

As a further aspect, this invention therefore provides a method of preparing a composition containing an amorphous undercooled phase which comprises a water-soluble or water-swellable substance in an amorphous form, said amorphous phase having a glass transition temperature of at least 20° C., much better at least 30° C. or 40° C., comprising the steps of drying an aqueous solution of a sugar which is capable of existing as a crystalline hydrate, to form a supersaturated amorphous composition with a residual moisture content, and allowing this sugar to crystallize, as the crystalline hydrate, from the supersaturated composition, so as to leave a residual amorphous phase, the amount of the said sugar in relation to the total water content of the composition after drying being such that the water content (if any) of the residual amorphous phase as a percentage by weight of that phase is a smaller percentage than the total water content of the composition expressed as a percentage of that composition.

The undercooled composition containing a hydratable sugar may be formed by drying an aqueous solution or suspension in vacuum or partial vacuum at ambient temperature of about 20° C. or at a slightly raised temperature, such as up to 40° C.

The composition could possibly be formed by freeze drying to yield an amorphous composition with some residual moisture content.

Yet another possibility is spray drying as disclosed in European published application 520748. In that process, an aqueous solution containing the material to be dried is sprayed into a hot gas stream. The droplets of spray are, dried to particles in a glassy or rubbery amorphous state as they travel in the hot gas stream, and are then collected from the gas stream.

The gas will generally be air but could be some other gas such as nitrogen.

Apparatus to carry out spray drying on a fairly small scale is available from various manufacturers. One is Drytec Ltd, Tonbridge, Kent who manufacture a pilot plant scale dryer. Another manufacturer is Lab-Plant Ltd of Longwood, Huddersfield, England who manufacture a laboratory scale dryer.

Process plant to carry out spray drying on a larger scale is also well known.

Referring to the drawing, in the laboratory scale spray-drying apparatus illustrated, air from the atmosphere is drawn in by a blower 10 and passes over an electric heater 12 after which the air passes down a main chamber 16. The aqueous mixture to be sprayed is drawn up from a supply vessel 18 by means of a peristaltic metering pump 20 and delivered to a spray nozzle 22 which discharges the aqueous mixture as a fine spray into the stream of hot air coming from the heater 12.

The droplets of spray are dried to solid powder form as they pass down within the main chamber 16. The powder is entrained in the air which has passed down the main chamber 16. This leaves by an exit tube 26 at one side delivering to a cyclone separator 28 which serves to remove entrained solid particles from the air stream. The solid particles which are separated from the air stream in this way are collected as the product in a detachable vessel 30 while the air passes out to atmosphere through an exhaust tube 32. Solids which stick to the wall of the main chamber fall into waste container 24.

A significant parameter in the operation of any spray drying apparatus is the temperature of the gas stream which is admitted to the main chamber and into which the spray is delivered. For the present invention this inlet temperature of the gas stream will generally exceed 80° C., will usually exceed 90° C. and may well lie in the range from 100 or 105° C. up to 250 or 300° C. Temperatures will often exceed 125° C.

The aqueous mixture which is delivered into the gas stream may typically contain from 10 up to 50 or even 250 grams per liter of material which will be dried to particles.

After drying to form a supersaturated amorphous composition, crystallization of the hydratable sugar can occur spontaneously if, before crystallization, the composition is above its glass transition temperature. If the glass transition temperature, before crystallization, is above ambient temperature or is close to it, it may be desirable to store the composition at a raised temperature for a time while crystallization occurs.

For this invention, crystallization should take place within a practical time scale. An appropriate temperature can promote the rate of crystallization. Such a temperature should desirably be chosen such that the amorphous composition is undercooled to a significant extent below the temperature at which the amorphous phase would exist as a saturated solution, yet at the same time is significantly above the glass transition temperature.

The rate at which sugars crystallize from a supersaturated solution varies. The speed at which a particular hydratable sugar crystallizes can be tested by keeping an amorphous composition under conditions where crystallization is expected, and periodically examining samples of the composition in a differential scanning calorimeter.

Additional moisture might then be absorbed by the amorphous phase during further processing. Another possibility is that during storage in a closed container, some moisture will leak into the container through an imperfect closure or seal. Moisture may also be admitted if the container is opened and reclosed.

Whichever way it enters, such moisture will tend to be absorbed by the amorphous phase, lowering its glass transition temperature. However, if the composition already contains some crystalline sugar hydrate and more of the same sugar in an amorphous state, this absorbed moisture will be removed by further crystallisation, so tending to maintain the glass transition temperature of the amorphous phase.

Crystallisation can be induced by adding a crystallisation seed. Typically this is a small crystal of the sugar hydrate.

If a composition contains sufficient of the hydratable sugar, crystallisation may well be arrested when the water in the amorphous phase has all, or almost all, been removed. The composition will then contain some crystalline sugar hydrate and some of the same sugar in an amorphous state.

EXAMPLES

Example 1

A 10% w/w solution of trehalose was dried to constant weight in ambient air (37° C., relative humidity 55%), at atmospheric pressure. After reaching constant weight, the residual moisture content of the dried mixture was measured by a coulometric Karl Fischer titration and found to be 18%. The dried composition (10 mg) was sealed in a stainless steel pan of a differential scanning calorimeter and cooled to −50° C. in the calorimeter (Perkin-Elmer DSC-2). The sample was then warmed at 5 deg/min and was found to undergo a glass transition at −20° C. The sample was further warmed and stored at room temperature overnight. It was then reexamined by DSC; the glass temperature had not changed. After storage at room temperature for one week, the sample was cooled once again to −50° C. in the calorimeter and subsequently heated at 5 deg/min to 140° C. A single thermal transition was observed, at 97° C., corresponding to the melting of the crystalline trehalose dihydrate. This demonstrates that crystallization can occur spontaneously during storage above the glass transition temperature. In this experiment there was an excess of moisture and so the conversion of trehalose to its crystalline dihydrate proceeded to the maximum extent possible, reaching an equilibrium state with the remaining water presumably existing as a very small amount of saturated solution of trehalose, in contact with the trehalose dihydrate crystals.

Example 2

80.362 mg of a 27.91% by weight aqueous solution of trehalose was placed in a stainless steel pan (Perkin-Elmer DSC) and air dried overnight at 25° C. under reduced pressure (800 mb) in a vacuum oven, provided with a cold trap condenser. The pan was reweighed; its weight after drying was 24.386 g. The remaining product was composed of 22.429 mg trehalose and 1.957 mg water, i.e. 8% residual moisture. The pan was sealed and placed in a Perkin-Elmer DSC-2 differential scanning calorimeter. The pan was cooled to −44° C. at a rate of 10 deg/min. It was then heated at the same rate to 140° C. and the heat flow curve was recorded. The only thermal feature observed was a step discontinuity in the heat flow, characteristic of a glass transition, centred on 31° C. This is consistent with the trehalose being present as an amorphous phase plasticised by the water.

Another calorimeter pan containing 22.208 mg of the identical trehalose solution, dried and sealed in a similar manner, was subsequently heated to 80–100° C. and kept at this temperature overnight. It was then cooled, placed in the differential scanning calorimeter, cooled to −50° C. and rewarmed to 130° C., the heating scan being recorded. Two thermal transitions were observed: a low-amplitude glass transition at 79.8° C. and a major melting process (endotherm) at 97° C., characteristic of the melting temperature of trehalose dihydrate. The sample was then once again cooled to −50° C. and rewarmed immediately, the heat flow curve being recorded. The only thermal feature observed was a high-amplitude glass transition at 32° C., as previously.

According to Green and Angel in "Phase Relations and Vitrification in saccharide-water solutions and the trehalose anomaly", J Phys Chem 93, 2880–2882 (1989), the glass transition of anhydrous trehalose occurs at 79° C. while that of trehalose with 8% residual moisture occurs at 32° C. Each gram of water requires 9.5 gram trehalose for complete conversion to crystalline dihydrate. The sample used in this example contained 1.98 mg water which would require 18.8 mg trehalose for complete conversion. Actually the sample contained 22.4 mg trehalose. Hence 3.6 mg anhydrous amorphous trehalose remained after crystallization of the dihydrate, consistent with the measured glass temperature of 79.8° C.

Example 3

The experimental procedure in Example 1 was repeated with raffinose which is known to form a pentahydrate, melting at 87° C. (which is below the glass transition temperature of anhydrous raffinose, at 103° C.). The sample used contained 85.924 mg of a 8.5% solution of raffinose. After drying at 25° C. (as above) the weight had decreased to 7.772 mg, of which 7.321 mg was raffinose and 0.451 mg water, i.e. 5.8% residual water.

The glass transition was observed at 40° C., showing the material to be completely amorphous. After heating the sealed pan at 80° C. overnight and rescanning over the temperature range 27–167° C., the only thermal transition detected was an endotherm at 84° C., consistent with the melting temperature of raffinose pentahydrate. Amorphous sugar in the sample could not be detected because the glass temperature of the amorphous phase lay above the melting temperature of the pentahydrate. The glass transition of the remaining anhydrous sugar (103° C.) could not be observed in the presence of the pentahydrate because of the pentahydrate's lower melting point, and the release of water from it into the amorphous phase as it melts.

Example 4

The procedure described in the previous Example was repeated with a sample which, after drying at 25° C., contained 6.406 mg of raffinose and 0.248 mg of water, i.e. 3.7% residual moisture, a large excess of sugar over that required to remove the water. A DSC scan revealed a glass transition at 63° C. After overnight heating at 80° C., the DSC scan showed the melting endotherm of the pentahydrate at 85° C. As in the previous example, the glass temperature of the remaining amorphous sugar could not be observed in the presence of the-pentahydrate. After cooling the melt a further DSC scan showed that the original glass temperature of 63° C. had been re-established, i.e. the melt had not recrystallised during cooling.

Example 5

A dried composition containing λ-DNA and trehalose was observed to have a glass transition at −12° C., while at 20° C. it had a viscoelastic consistency, consistent with an amorphous state above its glass transition temperature. After storage for some time, the preparation was observed to have a low-amplitude glass transition at 20° C., followed by a melting process at 82° C. (pure trehalose.2H$_2$O melts at 97° C.).

Example 6

In this and some subsequent Examples, glassy compositions were prepared containing lactate dehydrogenase (LDH) commercially available as Sigma type XI. Its suppliers recommend storage at temperatures below 0° C. European patent 383569 demonstrates that this enzyme can be stored at higher temperatures in a stable state, in an amorphous glass.

1.49 g of raffinose pentahydrate and 1.9 mg LDH were dissolved in 15 ml 0.01M phosphate buffer at pH7. 0.5 ml portions of this solution were dispensed into 20 glass vials of internal diameter 2.0 cm. The vials were loaded into a vacuum oven equilibrated at 60° C. and connected to a vacuum pump through a cold trap at −60° C. Drying began at 200 mbar pressure for one hour, followed by 18 hours drying at 2–4 mbar pressure. After drying, 12 vials were seen to contain amorphous material only, but 8 vials were seen to contain some crystalline material.

The glass transition temperature of material in vials with and without crystallisation was determined by DSC. Enzyme activity was determined by the procedure of Hatley, Franks and Mathias, Process Biochemistry, December 1987 page 170, which is also set out in European patent 383569.

In vials which contained amorphous material only, the material was found to have a glass transition temperature of 38.2° C. and an LDH activity of 7.1 units. In vials where. there was partial crystallisation, the LDH activity was higher and DSC showed an endotherm at 93° C. which was attributed to a glass transition.

This temperature is above the melting temperature of raffinose pentahydrate. We believe that the glassy amorphous material around the crystalline pentahydrate prevented it from melting at its normal melting temperature and effectively raised its melting point.

In this example only some of the vials displayed crystal formation because the initial formation of a crystal nucleus is a random process. In the vials where crystallisation occurred, it provided two beneficial effects. One of these was the removal of additional water from the remaining amorphous phase, thereby considerably increasing the glass transition temperature. This in turn increased the temperature at which the vials could be stored without degradation of the enzyme. Secondly, the removal of water into the crystalline pentahydrate had effectively shortened the time during which the enzyme-containing composition was exposed to a temperature higher than its glass transition temperature.

Example 7

LDH was dissolved in phosphate buffer solution containing raffinose and dried at 60° C. as in the previous example. After drying the vials were not sealed but were exposed either to ambient air or to a constant humidity environment (33% relative humidity over saturated magnesium chloride solution) at a temperature in the range 21–24° C. If there had been no crystallisation it would be expected that moisture would be absorbed from the atmosphere, leading to progressive reduction in the glass transition temperature of the amorphous phase and an eventual decline of enzyme activity.

Vials were assayed for enzyme activity after varying periods of storage. The measured activities were:

| Storage at ambient air (temperature range 21–24° C.) | |
| --- | --- |
| Days of storage | Activity per vial |
| 1 | 7.5 |
| 4 | 8.0 |
| 7 | 9.3 |
| 9 | 7.2 |
| 13 | 6.9 |

| Storage with exposure to 33% RH (temperature range 21–24° C.) | |
| --- | --- |
| Days of storage | Activity per vial |
| 1 | 8.8 |
| 4 | 9.6 |
| 7 | 8.6 |
| 9 | 7.6 |
| 13 | 8.9 |

In neither case was there any significant loss of enzyme activity. It appears that crystallisation of raffinose pentahydrate began in all vials, either during drying or very early in the storage period. This raised the glass transition temperature and also removed, by continuing crystallisation of raffinose pentahydrate, the atmospheric moisture absorbed by the composition thus maintaining the compositions in a glassy state so that the enzyme remains stable.

The LDH enzyme used in this Example could readily be replaced with other materials such as synthetic hormones or other synthetic organic chemicals.

Example 8

Four samples of raffinose pentahydrate were heated in small stainless steel pans until the crystals melted. On cooling, none of the samples recrystallised but all formed an amorphous raffinose solid (calculated moisture content 15% w/v). The pans were then exposed to water vapour by storage in a closed petri dish which contained a reservoir of water. Samples were periodically weighed to monitor moisture uptake, and inspected to see if crystallisation had occurred.

The following table sets out the weights of the samples after varying periods of time. Weights are expressed as a percentage of the initial weight of the sample.

Summary Table

| Exposure time (days) | Weight as % of initial | | | |
|---|---|---|---|---|
| | A | B | C | D |
| 1 | 175 | 178 | 166 | 179 |
| 2 | 203 | 207 | 193 | 206 |
| 5 | 224 | 229 | 138 | 222 |
| 6 | 225 | 220 | 119 | 224 |
| 7 | 229 | 215 | 100 | 226 |
| 8 | 237 | 236 | 100 | 218 |
| 9 | 235 | 238 | 100 | 182 |
| 12 | 243 | 215 | 100 | 109 |

After one day, all of the samples had absorbed a substantial amount of moisture from the atmosphere. For samples A and B this absorption of moisture continued and no crystallisation was observed. Sample C crystallised spontaneously after about five days. As crystallisation of the pentahydrate progressed, excess moisture was liberated to the atmosphere and the sample reverted to its initial weight. For sample D, crystallisation was deliberately induced after six days by the addition of a small crystal of raffinose pentahydrate. The weight was then observed to decline towards the initial weight as crystallisation of raffinose pentahydrate progressed. This demonstrates that crystallisation can be induced deliberately by means of an added seed crystal.

Example 9

50 ml of 10% w/v aqueous raffinose solution was spray-dried using an SD-05 spray drier from Lab-Plant Limited, Huddersfield, England. The hot air stream had an inlet temperature of 200° C. and the flow rate was the maximum available from the apparatus, approximately 50 m$^3$/hour. The raffinose solution was delivered into this airstream from a nozzle of 0.5 mm diameter at a flow rate of approximately 150 ml/hour and blown out of the nozzle using the minimum amount of compressed air, approximately 1.4 m$^3$/hour at a pressure of approximately 1 atmosphere above atmospheric.

2.06 gm of dried powder were collected. It was found to have a moisture content of 1.62% by weight. Most of this powder was stored in a 100 ml screwcap bottle while small samples (20–40 mg) were placed in calorimeter pans. A few very small seed crystals of raffinose pentahydrate were added to each pan. The glass transition temperature $T_g$ was measured immediately after spray drying, and after six days storage in the bottle. $T_g$ was also measured for the seeded samples after these were stored in the calorimeter pans for varying periods of time.

After measuring each glass transition temperature by DSC, the sample was progressively heated to a temperature which was sufficient to melt the raffinose. After this the sample was allowed to cool, forming an amorphous glass which contained all the moisture, $T_g$ was measured again. The results are set out in the following Table.

| Sample | Time | $T_g$ | $T_g$ (second measurement after melting and cooling) |
|---|---|---|---|
| Raffinose | immediately after drying | 92° C. | 89° C. |
| Raffinose seeded | 1 day after seeding | 91° C. | 89° C. |
| Raffinose seeded | 2 days after seeding | 91° C. | 89° C. |
| Raffinose seeded | 3 days after seeding | 84° C. | 81° C. |
| Raffinose seeded | 6 days after seeding | 96° C. | 82° C. |
| Raffinose (bulk) | 6 days after drying | 82° C. | 79° C. |

The declining values of $T_g$ in the second column show that the samples absorbed moisture during the six day period. However, the values in the first measurement of $T_g$ stayed approximately constant, showing that the absorbed moisture was taken out of the amorphous phase by further crystallisation of raffinose pentahydrate from that phase.

Example 10

An aqueous solution contained 8% w/v polyvinylpyrrolidone (PVP) and 2% w/v raffinose. It was spray dried under the conditions used in Example 9. $T_g$ of the collected powder was measured immediately and after four days. The results were:

| Sample | Time | $T_g$ | $T_g$ (second measurement after melting and cooling) |
|---|---|---|---|
| Raffinose + PVP alone | immediately after drying | 103° C. | 99° C. |
| Raffinose + PVP alone | 4 days after drying | 104° C. | 99° C. |

What is claimed is:

1. A composition suitable for improving the storage stability of a pharmaceutical compound or viable biological cells that are unstable at ambient temperatures, having an overall water content expressed as a percentage by weight of said composition, comprising
    (i) an amorphous, glassy phase having a glass transition temperature of at least 30° C. comprising a water soluble or water-swellable glass forming substance, and
    (ii) a crystalline sugar hydrate,
        wherein said composition is characterized by a glass transition temperature of the amorphous phase, which, when in the presence of said crystalline sugar hydrate, is greater than the glass transition temperature of said amorphous phase contained in a composition having the same overall water content and absent said crystalline sugar hydrate.

2. The composition of claim 1, wherein said amorphous phase comprises a water-soluble glass forming substance, and crystals of the sugar hydrate are embedded in the amorphous phase.

3. The composition of claim 1 wherein the amorphous phase comprises an amorphous sugar which is the same sugar as in the crystalline sugar hydrate.

4. The composition of claim 1 wherein said water-soluble or water-swellable glass forming substance is selected from the group consisting of carbohydrates, polyhydroxy compounds, natural polymers, and synthetic polymers which do not form a stable crystalline hydrate at temperatures in a range from 10° C. to 50° C.

5. The composition of claim 1 wherein said crystalline sugar hydrate is selected from the group consisting of dihydrates and polyhydrates, and wherein said water-soluble or water swellable glass forming substance is selected from the group consisting of carbohydrates, polyhydroxy compounds and synthetic polymers which do not form a stable crystalline dihydrate or polyhydrate at temperatures in a range from 10° C. to 50° C.

6. The composition of claim 1, wherein said amorphous phase further comprises a material selected from the group consisting of enzymes, non-enzymatic proteins, peptides, nucleosides, nucleotides, di- and oligonucleotides, biological cells and synthetic organic chemicals.

7. The composition of claim 1 having a total moisture content of at least about 1.6 weight percent.

8. The composition of claim 1, wherein said sugar is selected from the group consisting of trehalose, melibiose, melezitose, raffinose, mannotriose, and stachyose.

9. In a method of preparing a pharmaceutical composition suitable for improving the storage stability of a pharmaceutical compound or viable biological cells that are unstable at ambient temperatures and containing an amorphous, glassy phase having a glass transition temperature of at least 30° C. comprising a water-soluble or water-swellable glass-forming substance, comprising the steps of providing an aqueous solution containing said glass-forming substance, and drying said solution to form the pharmaceutical composition having a total water content, the improvement comprising providing in said solution a sugar capable of existing as a crystalline hydrate, and allowing said sugar to crystallize as said hydrate from the pharmaceutical composition to leave a residual amorphous phase, the amount of said sugar in the composition being sufficient, in relation to the total water content of the composition after drying, to extract water from said amorphous phase via crystallization of said sugar hydrate to thereby reduce the percentage content of water in said amorphous phase.

10. The method of claim 9, wherein said drying step comprises spraying said solution into a hot gas stream which is at a temperature in the range from 80° C. to 300° C., drying the solution to particles while they are travelling in the gas stream, separating the particles from the gas stream, and collecting said particles.

11. The method of claim 9 wherein the pharmaceutical composition formed in said drying step has a glass transition temperature below 30° C., and wherein crystallization of said sugar hydrate therefrom is effective to raise the glass transition temperature of said residual amorphous phase to above 30° C.

12. The method of claim 9, wherein said allowing comprises contacting said pharmaceutical composition with means to induce crystallization of said sugar hydrate.

13. The method of claim 9, wherein said residual amorphous phase comprises an amorphous sugar which is the same as in the crystalline sugar hydrate.

14. The method of claim 9, wherein said aqueous solution further comprises a material selected from the group consisting of enzymes, non-enzymatic proteins, peptides, nucleosides, nucleotides, di- and oligonucleotides, biological cells and synthetic organic chemicals, and which, as a result of said drying, forms a pharmaceutical composition comprising said material.

15. The composition of claim 9, wherein the amount of hydratable sugar relative to the total water content exceeds the stoichiometric ratio of sugar molecules to water molecules in the crystalline hydrate.

16. A method for increasing the storage stability of a moisture-containing pharmaceutical composition, comprising:

adding to a pharmaceutical composition comprising a pharmaceutical compound and a moisture-containing amorphous, glassy phase, a crytallizable hydratable sugar, wherein said amorphous phase has a glass transition temperature of at least 30° C. and comprises a water-soluble or water-swellable glass-forming substance, and whereby as a result of said adding, moisture is extracted from the amorphous phase via formation of a crystalline hydrate of said hydratable sugar, to thereby increase the glass transition temperature of the amorphous phase in said composition.

17. The composition of claim 16, wherein said composition has an overall moisture content of at least about 1.6 weight percent.

* * * * *

UNITED STATES PATENT AND TRADEMARK OFFICE
CERTIFICATE OF CORRECTION

PATENT NO.    : 6,071,428
DATED         : June 6, 2000
INVENTOR(S)   : Felix Franks et al.

It is certified that error appears in the above-identified patent and that said Letters Patent is hereby corrected as shown below:

Column 16,
Line 23, replace "composition" with -- method --.
Line 43, replace "composition" with -- method --.

Signed and Sealed this

Ninth Day of September, 2003

JAMES E. ROGAN
*Director of the United States Patent and Trademark Office*